United States Patent
Carlsson

(10) Patent No.: US 9,464,309 B2
(45) Date of Patent: Oct. 11, 2016

(54) METHODS FOR RECOVERING PEPTIDES/AMINO ACIDS AND OIL/FAT FROM ONE OR MORE PROTEIN-CONTAINING RAW MATERIALS, AND PRODUCTS PRODUCED BY THE METHODS

(71) Applicant: Zymtech Production AS, Lesja (NO)

(72) Inventor: Tomas Carlsson, Lesja (NO)

(73) Assignee: ZYMTECH HOLDING AG, Zug (CH)

( * ) Notice: Subject to any disclaimer, the term of this patent is extended or adjusted under 35 U.S.C. 154(b) by 0 days.

(21) Appl. No.: 14/076,251

(22) Filed: Nov. 10, 2013

(65) Prior Publication Data

US 2014/0066359 A1   Mar. 6, 2014

Related U.S. Application Data

(60) Continuation of application No. 13/356,240, filed on Jan. 23, 2012, now abandoned, which is a continuation of application No. 12/797,506, filed on Jun. 9, 2010, now abandoned, which is a division of application No. 10/523,151, filed as application No. PCT/NO03/00260 on Jul. 29, 2003, now abandoned.

(30) Foreign Application Priority Data

Jul. 29, 2002 (NO) ................................ 20023601
Jul. 29, 2002 (NO) ................................ 20023602
Jul. 29, 2002 (NO) ................................ 20023603

(51) Int. Cl.
| | |
|---|---|
| C12P 21/06 | (2006.01) |
| C11B 3/00 | (2006.01) |
| A61K 38/01 | (2006.01) |
| A23J 1/04 | (2006.01) |
| A23J 3/34 | (2006.01) |
| B01D 61/00 | (2006.01) |
| B01D 61/02 | (2006.01) |
| C01B 25/32 | (2006.01) |
| C11B 1/10 | (2006.01) |

(52) U.S. Cl.
CPC  *C12P 21/06* (2013.01); *A23J 1/04* (2013.01); *A23J 3/341* (2013.01); *A23K 20/147* (2016.05); *A61K 38/01* (2013.01); *B01D 61/002* (2013.01); *B01D 61/022* (2013.01); *C01B 25/32* (2013.01); *C11B 1/10* (2013.01); *C11B 3/003* (2013.01); *A23V 2002/00* (2013.01); *B01D 2315/10* (2013.01)

(58) Field of Classification Search
CPC ........ C12P 21/06; A61K 38/01; C11B 3/003
USPC ............................................................ 514/1.1
See application file for complete search history.

(56) References Cited

U.S. PATENT DOCUMENTS

| | | |
|---|---|---|
| 4,473,589 A | 9/1984 | Freeman et al. |
| 4,579,660 A | 4/1986 | Toushek et al. |
| 4,874,893 A | 10/1989 | Flork |
| 5,053,234 A | 10/1991 | Anderson et al. |
| 5,352,476 A | 10/1994 | Brule et al. |
| 5,356,637 A | 10/1994 | Loosen et al. |
| 5,532,007 A | 7/1996 | Pedersen et al. |
| 5,589,508 A * | 12/1996 | Schlotzer ............... A61K 31/20 514/560 |
| 5,698,724 A | 12/1997 | Anderson et al. |
| 5,985,337 A | 11/1999 | Blortz et al. |
| 6,221,423 B1 | 4/2001 | Cho et al. |
| 6,323,354 B1 | 11/2001 | Moore |
| 6,372,282 B1 | 4/2002 | Edens et al. |
| 6,747,001 B2 | 6/2004 | Raa et al. |
| 6,770,199 B1 | 8/2004 | Taylor et al. |
| 6,841,171 B1 | 1/2005 | Durand et al. |
| 6,860,998 B1 | 3/2005 | Wilde |
| 6,875,456 B2 | 4/2005 | Delest et al. |
| 6,960,451 B2 | 11/2005 | Pyntikov et al. |
| 2004/0038391 A1 | 2/2004 | Pyntikov et al. |
| 2004/0192981 A1 | 9/2004 | Appel et al. |

FOREIGN PATENT DOCUMENTS

| | | |
|---|---|---|
| CA | 2205712 | 6/1998 |
| EP | 1312611 | 5/2003 |
| EP | 1227736 | 1/2004 |
| FR | 2168259 | 8/1973 |
| JP | 2-97409 | 4/1990 |
| RU | 1559466 | 10/1996 |

(Continued)

OTHER PUBLICATIONS

W02005/018337—Machine Translation.*

(Continued)

*Primary Examiner* — Hamid R Badr
(74) *Attorney, Agent, or Firm* — VLP Law Group LLP; Richard G. A. Bone

(57) ABSTRACT

According to a first aspect, hydrolysis of a protein-containing raw material and separation of amino acids/peptides is carried out, wherein the hydrolysis is effected by using the endogenous enzymes of the protein-containing raw material. The hydrolysate is passed through a membrane filter, wherein peptide/amino acids follow a permeate stream, while the active enzymes continuously break down any protein residues that are deposited on the membrane surface. The enzymes are passed together with retentate back to the hydrolysis. Furthermore, an amino acid and peptide product and an oil product are described and the use thereof is disclosed.

14 Claims, 3 Drawing Sheets

(56) References Cited

FOREIGN PATENT DOCUMENTS

| | | | |
|---|---|---|---|
| RU | 1755417 | 11/1996 | |
| RU | 2103360 | 1/1998 | |
| RU | WO2005018337 | * 3/2005 | ............... A23J 1/04 |
| WO | 9118520 | 12/1991 | |
| WO | 9739130 | 10/1997 | |
| WO | 9920770 | 4/1999 | |
| WO | 0128353 | 4/2001 | |
| WO | 0184949 | 11/2001 | |
| WO | 0219837 | 3/2002 | |
| WO | 0232231 | 4/2002 | |
| WO | 02065848 | 8/2002 | |
| WO | 02078461 | 10/2002 | |

OTHER PUBLICATIONS

Arends, J. et al. J. Crystal Growth. 46: 213-220 (1979).*

Kim, S. et al., 2011. Isolation and characterization of antioxidative peptides from gelatin hydrolysate of Alaska Pollack skin. J. Agric. Food Chem. 49: 1984-1989.

* cited by examiner

METHODS FOR RECOVERING PEPTIDES/AMINO ACIDS AND OIL/FAT FROM ONE OR MORE PROTEIN-CONTAINING RAW MATERIALS, AND PRODUCTS PRODUCED BY THE METHODS

CLAIM OF PRIORITY

This application is a continuation of U.S. application Ser. No. 13/356,240, filed Jan. 23, 2012 and now abandoned, which is a continuation of U.S. application Ser. No. 12/797,506, filed Jun. 9, 2010 and now abandoned, which is a divisional of U.S. application Ser. No. 10/523,151 now abandoned, which is a 371 of international application serial no. PCT/NO03/00260 having an international filing date of Jul. 29, 2003, and which claims the benefit of Norway application serial nos. 2002/3601 filed Jul. 29, 2002, 2002/3602 filed Jul. 29, 2002, and 2002/3603 filed Jul. 29, 2002. The disclosure of each of these applications is incorporated herein by reference in its entirety.

FIELD OF INVENTION

The present invention relates to aspects concerning:

a) a method for producing a protein-free product containing peptides, free amino acids and minerals from raw animal or aquatic materials, and the products and their use as animal feed and/or in products for the biotechnological, pharmaceutical and food processing industries. An oil product that is a result of the aforementioned method is also described.

b) a method for producing a protein product enriched with free amino acids and short peptides, the product obtained and its use as animal feed and/or in products for veterinary medical use and in the food processing industry. An oil product that is the result of the aforementioned method is also described.

c) a method for recovering peptides, free amino acids and minerals from raw animal or aquatic materials.

In the industry it is known to produce peptides and amino acids by acid hydrolysis, and using biotechnological and/or chemical/technical, both natural and synthesised, concentrated enzymes. The present invention is a way of using the naturally occurring decomposing enzymes from raw animal or aquatic materials in an industrial process that yields a product of pharmaceutical quality, biotechnological quality, foodstuff quality or veterinary medical quality.

By the term "pharmaceutical quality" is meant products for intravenous use and products that are classified as medicine for humans and animals or natural medicine.

By the term "biotechnological quality" is meant products that can be used, for example, as culture media or catalysts in the culturing of cells, bacteria, fungi and algae.

By the term "foodstuff quality" is meant products that are used for human consumption either as an additive or as an independent product.

By the term "veterinary medical quality" is meant products that are classified as medicine for animals.

The invention may optionally also be used to produce feed products in the form of an additive or as independent products.

BACKGROUND

Amino acids and peptides are well known in the pharmaceutical, natural medicine and veterinary medical industries as constituents of products such as intravenous foods and as special foods for relieving certain trauma. To date, it is chiefly extracts from blood plasma and protein hydrolysate produced using pancreatic enzymes from pigs and calves that have been used in this area. The invention provides the pharmaceutical industry with the possibility of obtaining a supply of amino acids and peptides of a hitherto unknown quality.

Amino acids and ultrashort peptides are also used for biotechnological processes, for example, when a highly potent culture medium is to be produced. A limitation for all industry that cultivates single cell organisms or cell substrates from higher organisms is the supply of culture media of adequate quality. Defects or a high price are limiting factors. Moreover, amino acids or peptides produced by biotechnological methods generally contain growth-inhibiting substances which can be avoided by using the products produced by the method of the invention. The combination of spectra of natural amino acids and biological micronutrients/minerals produced by the process described yields a unique product for the preparation of culture media for the biotechnological industry. Moreover, the technique can recycle proteins from many types of cultures back to amino acids and peptides which can then be reused.

Peptides/amino acids are used in the food processing industry as binders, emulsifiers, flavouring additives and the like. The uses are considerable and are increasing. The most used peptides and amino acids in the food processing industry derive from soya beans and milk. Amino acids and peptides from soya and milk in particular are known for causing allergenic reactions which can only be avoided by using another peptide/amino acid composition which does not derive from these sources, or a peptide/amino acid composition from soya or milk that has been sufficiently modified so as not to cause these reactions. Therefore, there is a great need for a method which provides a composition of amino acids and peptides that can also derive from soya and/or milk, but which do not cause allergenic reactions. Products from most animal sources have not attained the same degree of utilisation as there are no extraction techniques that maintain the functionality of the product whilst removing undesired quality-reducing components such as salt and fat.

Many different compositions of proteins, peptides and amino acids deriving from different sources are used in the production of animal feed. The composition of the peptides, the amino acids and the proteins is also very important in the production of feed as the animals' growth potential is dependent upon a balanced feed intake. Therefore, in this area too, there is a great need for a method which produces any desired composition that provides optimal growth conditions for the animals.

In the following the term "endogenous" enzymes is used as a term for the enzymes originating within the protein product as opposed to the "exogenous" enzymes which are extraneous enzymes added to the raw protein material during traditional hydrolysis. One example of an "exogenous" enzyme is "Deterzyme APY", which is a bacterial protease (E.C. 3.4.21) prepared by controlled fermentation of *Bacillus alcalophilus*, and which can be purchased from a number of suppliers. The term "endogenous" enzymes is also used to mean enzymes extracted from other similar natural enzyme materials or raw materials, preferably from cold-blooded animals.

The term "hydrolysate" is used in the text below as a designation for the raw materials that are being processed, i.e., that the warmed and pH-adjusted mixture of raw material and water constitutes the hydrolysate. This applies in particular to aspects a) and b) of the invention.

There are a number of patents in the field of the invention, as for example RU 2103360 which describes a nutrient medium for culturing eucaryotic cells and a method for preparing a hydrolysate from fish internals which is prepared by proteolytic hydrolysis. This hydrolysis process is carried out at a high pH adjusted with sodium hydroxide, by using temperature inactivation, filtering and drying in which the fish offal is mixed with distilled water in a ratio of 1:1. The hydrolysis is carried out at a temperature of +40°-+42° C. until a weight percentage of amino nitrogen of 5.5-6-5% and a weight percentage of free amino acids of 50-60% are obtained.

SU 1755417 also discloses a method for the production of hydrolysates from raw fish material in a fermenter to which a fermentation preparation is added, followed by a filtering and drying of the hydrolysate produced, wherein non-crushed raw material is used that is fed periodically into the fermenter.

RU 1559466 describes a method for the production of hydrolysates, which requires the crushing of fish products or scrap from the processing thereof, mixing with water, heating the mixture, adding a proteolytic fermentation preparation, fermenting, filtering and drying, wherein raw materials and water are mixed in a ratio of 2:1-1:1, and heated to a temperature of +40°-+45° C., whilst fermentation is carried out over a period of 0.5-2.5 hours using the exogenous enzyme protosubtilin G3x.

Reference is also made to FR 2168259 which describes an enzymatic hydrolysis of fish proteins that is carried out by crushing fresh fish into a fine paste without adding water. Exogenous enzymes are added and the paste is hydrolysed for about 15 hours depending upon desired solubility. The product is stabilised for 5-20 minutes at +90°-+100° C., and is filtered, pasteurised and centrifuged. The process yields products of a high nutritional value.

As shown in the above, different techniques are known for releasing proteins, peptides and amino acids from fish which are suitable for food production. Moreover, it is also known to prepare oil/fat from raw materials from both plant and animal sources.

SUMMARY

According to aspect a), the object of the present invention is to provide a method for producing a protein-fee protein hydrolysate based on the use of natural enzymes without the addition of any non-natural substances. This is in contrast to other methods which use enzymes from many different sources, such as from bacterial cultures or the like.

It is also an object that the process should provide a product that is completely free of protein and DNA and other allergenic substances and that this is done without adversely affecting the utilisation of the raw materials. The method is also intended to reduce the fat in the end product to such a low level that the disadvantages of using raw fish materials are eliminated. It is intended to produce a product that can be used in many different areas where the use of products produced by known methods has been limited or made impossible because of their fat content.

It is also an object to utilise the raw materials to the full and to ensure that the environmental stresses associated with the production are minimal.

Thus, according to aspect a) of the invention there is provided a method for recovering peptides/amino acids and oil/fat from protein-containing raw materials characterised in that it comprises the following steps:
 a. grinding the raw materials;
 b. heating the ground raw materials to a temperature in the range of 40-62° C., preferably 45-58° C.;
 c. optionally before and/or after the heating step, separating oil/fat from the raw materials in order to obtain a first oil product;
 d. adding water, the water having approximately the same or the same temperature as the raw materials, and wherein the pH of the water is adjusted by adding calcium;
 e. hydrolysing the raw materials with endogenous enzymes in order to prepare a hydrolysate:
 f. optionally during the hydrolysation step, adding a pH adjuster in order to maintain the desired pH value of the hydrolysate;
 g. heating the hydrolysate to 75-100° C., preferably 85-95° C.;
 h. removing large particles from the hydrolysate, including non-hydrolysed proteins, which can be returned to the hydrolysis step;
 i. optionally separating off fat/oil in order to obtain a second oil product;
 j. coagulating the proteins;
 k. removing the coagulated proteins;
 l. optionally separating off fat/oil in order to obtain a third oil product;
 m. optionally concentrating the remaining amino acids and short peptides; and
 n. optionally drying the concentrate in order to obtain dry short peptides and amino acids.

Preferred embodiments of the method according to aspect a) of the invention are set forth hereinbelow.

The method according to the invention facilitates the production of a peptide and amino acid product having a low fat content, preferably less than 0.1%. Furthermore, the produced product contains natural minerals of biological origin. The salt content of the product is less than 1%.

The invention also comprises a use of one of the methods according to the invention for producing a biotechnological product, a pharmaceutical product, a food product, and a feed product.

The invention also comprises the use of the method according to the invention for producing hydroxyapatite.

The invention also makes possible the production of amino acids/peptides prepared by the method according to the invention.

There is also provided hydroxyapatite produced by the method according to the invention and characterised in that it does not contain any allergens and DNA traces.

In addition, there is also provided an oil produced by the method according to the invention and characterised in that it does not contain allergens and DNA traces.

On the one hand, the present invention solves the problem of producing products with a broad quality spectrum which varies from their use for food products to their use in products that are to meet the requirements for pharmaceuticals and the like, for instance.

On the other hand, the present invention solves this problem by using the endogenous enzymes of the raw materials and adapting the production conditions to these enzymes.

The process differs essentially from the prior art hydrolysis processes in that it may be carried out or is carried out:
 without any additives, such as chloroform, in order to prevent unwanted bacterial growth;
 without the addition of sodium hydroxide;

with the possibility of hot and cold recovery of oil/fat;

with the possibility of controlling the spectrum of free amino acids and peptides in the end product in selecting raw materials for the process by choosing specific raw materials;

with the possibility of controlling the result of the process, as regards the amino acid and peptide composition by means of the applied process parameters such as temperature and pH;

without the addition of acid during the hydrolysis process;

with a flexible combination of different raw materials;

by using an adapted concentration step for separating off the product fractions; and in that by removing proteins and large peptides that are not fully hydrolysed through coagulation;

by filtering and separating off the coagulated proteins, through the use of an adapted concentration technique, and by using a shorter time for hydrolysis, it yields a product containing minerals and micronutrients of biological origin.

According to aspect b), the object of the present invention is to provide a method for producing a protein product containing free amino acids and short and long peptides based on the use of natural enzymes without the addition of any non-natural substances. This is in contrast to other methods which use enzymes from many different sources, such as from bacterial cultures and the like.

Furthermore, the method is also intended to reduce the fat in the end product to such a low level that the disadvantages of using raw fish materials are eliminated. It is intended to provide a product that is capable of use in many different areas where the use of products produced by known methods has been limited or made impossible because of their fat content.

Furthermore, it is an object to utilise the raw materials to the full and to ensure that the environmental stresses associated with the production are minimal.

Thus there is provided a method for recovering a protein product containing peptides and free amino acids from one or more protein-containing raw products, characterised in that it comprises the following steps:

a. grinding the raw materials;
b. heating the ground raw material to temperatures in the range of 40-62° C., preferably 45-58° C.;
c. optionally before and/or after the heating step, separating oil/fat from the raw materials in order to obtain a first oil product;
d. adding water, the water having approximately the same or the same temperature as the raw materials, and wherein the pH value of the water is adjusted by adding calcium;
e. hydrolysing the raw materials with endogenous enzymes in order to prepare a hydrolysate;
f. optionally during the hydrolysis step, adding a pH adjuster, for example, calcium, nitrogen or bone meal, in order to maintain the desired pH value of the hydrolysate. A caustic solution is not used for pH adjustment;
g. heating the hydrolysate to 75-100° C., preferably 85-95° C.;
h. removing large particles from the hydrolysate including non-hydrolysed proteins;
i. optionally separating off fat/oil in order to obtain a second oil product;
j. removing the proteins and long peptides;
k. concentrating the remaining amino acids and peptides;
l. returning proteins and long peptides to the concentrate in order to obtain a protein product; and
m. optionally drying the protein product in order to obtain a dried product containing proteins, free amino acids and short and long peptides:

Preferred embodiments of the method according to aspect b) of the invention are set forth hereinbelow.

The protein product produced by the method of the invention is characterised in that it contains 5-95% by weight of free amino acids, preferably 30-60% by weight, whilst the remaining 95-5% comprises proteins and minerals, the minerals being natural minerals of biological origin.

Furthermore, the protein product has a fat content of less than 0.5% by weight and a low salt content, typically less than 1% by weight.

The invention also comprises a use of the method according to the invention for producing a veterinary medical product, a food product and a feed product.

There is also provided an oil, characterised in that it is the first oil product produced by the method according to the invention and is of a foodstuff quality.

On the one hand, the present invention according to aspect b), among others, solves the problem of providing products having a broad quality spectrum which varies from their use for food production to the use of the products of pharmaceutical quality.

On the other hand, according to aspect b), the present invention solves this problem by using the endogenous enzymes of the fish and adapting the production conditions to these enzymes.

The process differs essentially from previously known hydrolysis processes in that it may be carried out/is carried out:

without additives, such as chloroform, in order to prevent undesirable bacterial growth;

without the addition of sodium hydroxide;

with the possibility of hot and cold recovery of oil/fat;

with the possibility of controlling the spectrum of free amino acids and peptides in the end product in selecting raw materials for the process by choosing specific raw materials;

with the possibility of controlling the result of the process, as regards amino acid and peptide composition, by means of the applied process parameters such as temperature and pH;

without the addition of acid during the hydrolysis;

with a flexible combination of different raw materials;

by using an adapted concentration step for separating off product fractions; and in that through the use of adapted concentration technique; and by using a shorter time for hydrolysis; it yields a product that contains minerals and micronutrients of biological origin.

The methods according to aspects a) and b) that are described are a natural hydrolysis of proteins with the purpose of obtaining dried end products having different compositions of short peptides and free amino acids. The process yields finished products that contain from 5% to 100% free amino acids, optionally without proteins and long peptides (aspect (a)). In addition, the methods describe the recovery of oils/fat.

According to aspect c) of the present invention, the object is to provide a method for producing a protein hydrolysate based on the use of natural enzymes without the addition of any non-natural substances. This is in contrast to other methods that use enzymes from many different sources such as bacterial cultures and the like.

Furthermore, it is an object that the process according to aspect c) should provide a product that is completely free of protein and DNA and other allergenic substances, and that this is done without adversely affecting the utilisation of the raw materials. The method is also intended to reduce the fat in the end product to such a low level that the disadvantages of using raw fish materials are eliminated. It is intended to produce a product that can be used in many different areas where the use of products produced by known methods has been limited or made impossible because of their fat content.

It is also an object to utilise the raw materials to the full and ensure that the environmental stresses associated with the production are minimal.

Thus, according to aspect c) of the invention there is provided a method for recovering peptides/amino acids and oil/fat from a protein-containing raw material, characterised in that it comprises the following steps:

a. grinding the raw materials;
b. heating the ground raw materials to temperatures in the range of 40-62° C., preferably 45-58° C.;
c. optionally before and/or after separating oil/fat from the raw material in order to obtain a first oil product;
d. adding water which has approximately the same or the same temperature as the raw material, and wherein the pH of the water is adjusted by adding calcium;
e. hydrolysing the raw materials with endogenous enzymes or enzymes from similar raw materials, preferably from cold-blooded species, in order to prepare a hydrolysate;
f. optionally during the hydrolysation step adding a pH adjuster in order to maintain the desired pH value of the hydrolysate;
g. removing solid particles and non-hydrolysed proteins which can be returned to the hydrolysis from the hydrolysate;
h. periodically or continually separating off fat/oil in order to obtain a second oil product;
i. optionally treating the hydrolysate against microorganism growth, preferably with UV treatment;
j. separating off the molecular weight fraction of peptides/amino acids desired by membrane filtration, preferably of crossflow type;
k. routing the portions of the hydrolysate that do not penetrate the membrane filter in point j back to the hydrolysis in step e;
l. concentrating and optionally drying the permeate in order to obtain peptides/amino acids;
m. wholly or partly returning the distillate from the concentration step to the permeate side of the membrane filter.

Preferred embodiments of the method according to the invention are set forth hereinbelow.

The term "membrane filter" is used in this context to mean membrane-like filters such membrane filters, osmotic filters, ultrafilters, electrostatic filters, crossflow filters and the like. These should preferably be characterised by a cut-off value of less than or equal to 10,000 Daltons.

Moreover, there is provided a method for the hydrolysis of one or more protein-containing raw materials and the separation of amino acids/peptides, which is characterised in that the hydrolysis is carried out using the endogenous enzymes of the protein-containing raw material or materials and that the hydrolysate is passed through a membrane filter, wherein peptides/amino acids follow a permeate stream, whilst the active enzymes continuously break down any protein residues that are deposited on the membrane surface and that the enzymes are passed together with the retentate back to the hydrolysis.

Another feature of the invention is a method for separating peptides and amino acids from a hydrolysis mixture, which is characterised in that the hydrolysis mixture comprising active enzymes, amino acids, peptides and non-converted proteins is passed through a membrane filter, wherein amino acids and any peptides are filtered off and the active enzymes present ensure that proteins deposited on the membrane filter are broken down.

The invention also comprises a use of one of the methods according to the invention for producing a pharmaceutical product, a biotechnological product, a food product and a feed product.

The invention also comprises the use of the method according to the invention for producing hydroxyapatite.

Furthermore, there are provided amino acids/peptides produced by the method according to the invention and characterised in that they do not contain allergens and DNA traces.

There is also provided an oil produced by the method according to the invention and characterised in that it does not contain allergens and DNA traces.

Lastly, there is provided hydroxyapatite produced by the method according to the invention and characterised in that it does not contain allergens and DNA traces.

On the one hand, the present invention according to aspect c) solves the problem of providing products having a broad quality spectrum which varies from their use for food production to their use in products that are to satisfy the requirements for pharmaceuticals and the like, for instance.

On the other hand, the present invention solves this problem by using the endogenous enzymes of the raw materials and adapting the production conditions to these enzymes.

This aspect c) of the invention combines the use of endogenous enzymes with a technique for recovering specific size-determined molecules from simple amino acids to large peptides of slightly less than 10,000 Daltons.

The invention involves retaining the enzymes in the fermentation process whilst the amino acids and peptides released are separated off.

The invention also means that the hydrolysis process can be run continuously with the addition of more raw materials during the process.

The process differs essentially from prior art enzymation processes in that it is carried out or may be carried out:
without additives, such as chloroform in order to prevent undesirable bacterial growth;
without the addition of sodium hydroxide;
with the possibility of hot and cold recovery of protein-free and sterile marine oil/fat;
with the possibility of controlling the spectrum of free amino acids and peptides in the end product in selecting raw materials for the process by choosing of specific raw materials;
with the possibility of controlling the result of the process, as regards amino acid and peptide composition, by means of the applied process parameters such as temperature and pH;
without the addition of acid;
with a flexible combination of different raw materials;
by using an adapted concentration step for separating off product fractions; and in that
by using a continuous enzyme degradation process;
without coagulation of proteins and/or peptides when using acid or a base; and
by size grading of the peptides produced;
it yields a product that contains minerals and micronutrients of biological origin.

Thus, there is provided a method for recovering peptide/amino acids, minerals and oil or fat from protein materials preferably of aquatic origin.

The prior art differs from the present invention by means of a basically different method for preparing fish proteins, which are also found in different fractions containing peptides and amino acids. The production conditions also differ essentially from this art and with the present invention the use of exogenous enzymes is avoided. In addition, as also taught in the previously mentioned cited material, marine oils/fat of high quality are produced by the present invention by developing a different specific method that is not described in the prior art.

The method described is a natural enzymation of proteins with the object of obtaining dried end products or liquid products containing different compositions of peptides and free amino acids. The process yields finished products which optionally contain from 5% to 100% free amino acids. The product does not contain allergens and DNA traces. There are only very small amounts of fat, typically less than 0.1%, and biological micronutrients. The method according to the invention gives a product that is fully useful as culture media for all types of cultures, including cells from higher organisms.

The present invention permits a method without the use of sodium hydroxide which can result in problems in the production of amino acids and peptides on an industrial scale. Moreover, the water ratio can be varied to a greater extent than in the prior art, and the percentage by weight of free amino acids is also in a larger range.

In comparison with this art, both crushed and non-crushed starting material are used in the present invention, and there is no addition of a fermentation preparation, but natural enzymes are used that are already present in the raw material. Thus, the endogenous enzymes of the raw protein material are used and this results in a simpler, more stable and less expensive way of carrying out the hydrolysis. In addition, the conditions must be directly adapted to the activity conditions of the endogenous enzymes which are also different from the prior art.

Another problem found in this industry in that exogenous enzymes are expensive and may be of varying quality. The present invention avoids this problem by a recycling of the endogenous enzymes.

Furthermore, the active enzymes have a specific cleaning function. Since they are retained in the filter, these enzymes act on non-filtered proteins and peptides. The enzymes cause the breakdown of these materials and therefore the filter has a longer life compared with the traditional filtering processes used in hitherto known hydrolysis processes. This is a great advantage as regards the costs, life time and efficiency of the filters, the quality of the products and the level of utilisation of the system or process.

In addition, the method describes the recovery of oils/fat and solids. One of the solids that can be obtained by the method according to the invention is hydroxyapatite. Hydroxyapatite is used, for example, in biochromatography and other biological separation processes, in NMR and other detection processes, and is thus a commercially interesting by-product of the process.

Choice of technique and process parameters will determine what end product is obtained. In this way, it will be possible to adapt products to the customer's requirements.

DETAILED DESCRIPTION OF THE PREFERRED EMBODIMENTS

Figure 1:
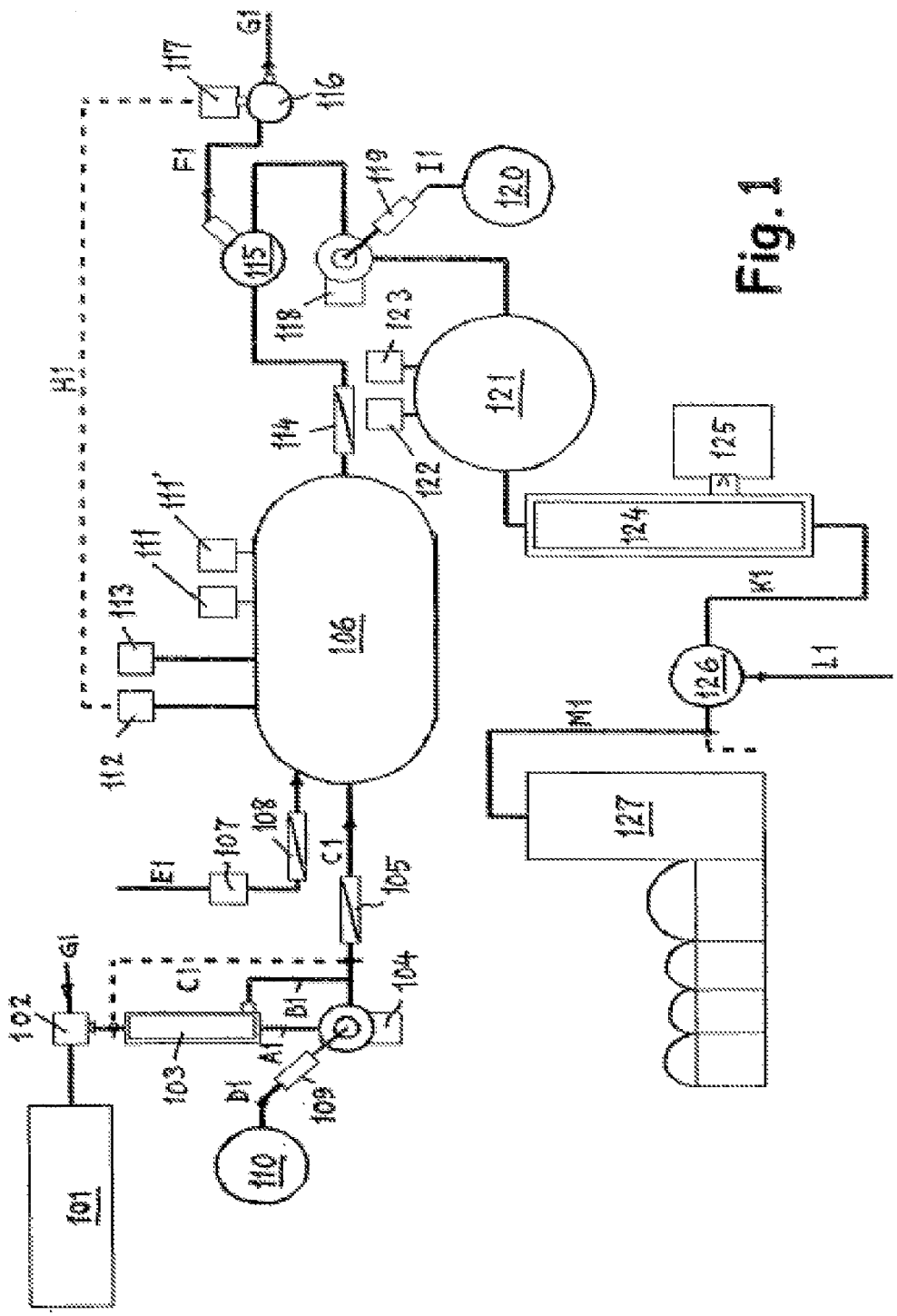
FIG. 1 shows a first embodiment of a plant in which the hydrolysis process according to aspect a) of the invention is used.

The embodiments of the methods according to aspects a) and b) of the invention respectively are explained in more detail in the following with reference to FIGS. 1 and 2 respectively.

The raw materials are pumped in from tank 101; 201 through a grinding system 102; 202 which gives the desired combination of the raw materials.

Oil/fat from the raw materials can be recovered before the enzyme process is started. Here, for example, a cold recovery of the oil could be used. It is also possible not to remove the oil before enzymation. In that case, the raw materials are pumped straight to the heat exchanger 105; 205 in by-pass stream D1; D2.

Cold recovery of oil can be carried out by:
1. centrifuging the raw materials and separating liquid and solid particles into two different fractions in, for example, a decanter centrifuge 103; 203;
2. separating the oil from the liquid phase stream A1; A2 using, for example, a separator 104; 204;
3. mixing the solid phase stream B1; B2 and the heavy phase from the separation and pumping stream C1; C2 to the fermenter;
4. the oil phase from the separation stream D1; D2 can be pumped to tank 110; 210 via a sterile filter 109; 209 and thus does not require further refinement in order to attain foodstuff quality.

The materials can be pumped via either an "in-line" continuous heat exchanger 105; 205 or a batch working heat exchanger to the fermentation tank 106; 206. The fermentation tank can also be used for heating if this is not done in a heat exchanger before the materials are pumped in. Added to the raw materials is a warmed and pH-adjusted water stream E1; E2 which is heated via a heat exchanger 108; 208 to approximately the temperature at which the fermentation is to take place. The adjustment of pH is preferably done by passing the water through a filter medium that releases calcium 107; 207.

Temperature and pH are monitored by sensors 111, 111'; 211, 211', or in another manner, in the fermenter during the process. Adjustment to the desired pH is effected during the process preferably using bone meal or calcium that is added from storage tank 112, 212. Nitrogen 113, 213 may also be used for adjusting pH during the process.

When the enzymation is finished, the hydrolysate is heated preferably via a heat exchanger 114; 214, so that the enzymes are inactivated.

If the hydrolysate contains bones or other solid particles, these are removed preferably by using a screen device 115; 215. The solid particles, stream F1; F2, can be separated into two or more fractions by means of flotation 116; 216. The heavy fraction 117; 217 consists of bones (hydroxyapatite) that can be dried and/or used prior to pH adjustment, cf. stream H1; H2. The light fractions, stream G1; G2, are primarily proteins that are not hydrolysed.

These light fractions G1 can be returned to the grinder 102; as shown in FIG. 1, and used as raw material for a new hydrolysis process or removed as a by-product.

Figure 2:
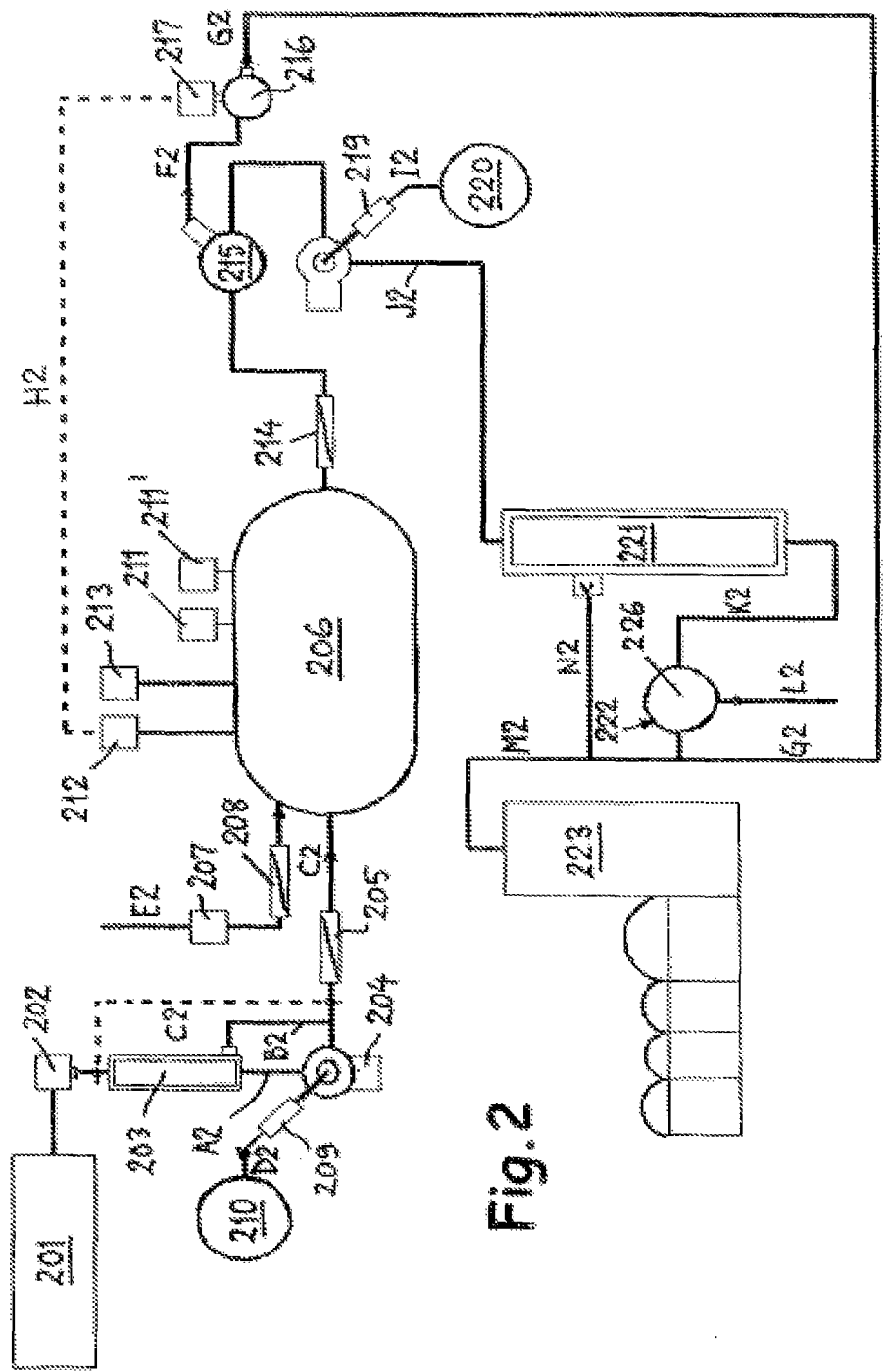
FIG. 2 shows a second embodiment of a plant in which the hydrolysis process according to aspect b) of the invention is used.

As shown in FIG. 2, the light fractions G2 according to aspect b) of the invention can be passed on separately and mixed with a concentrate from the concentrator 222. Alternatively, they can be dried as a separate product.

The fat that remains after the first fat separation is separated off using, for example, a three-phase separator 118; 218. The oil/fat stream I1; I2 is filtered in the filter 119; 219 and can be taken to the tank 120; 220 for optional subsequent further processing or the like.

As shown in FIG. 1, the hydrolysate, stream J1, is passed to a mixing tank 121 wherein acid 122 (preferably phosphoric acid) is added until the pH<5. Then calcium 123 is added so that long peptides and proteins agglomerate. The proteins and calcium/calcium phosphate are separated off using a centrifuge 124 and are passed to a tank 125. This by-product can be dried at a high temperature so that all protein residues are burned off.

The protein-free hydrolysate stream K1 is concentrated preferably in a vacuum evaporator 126. The condensate, stream L1, can be used as additive water, stream E1. The concentrate, stream M1, can be dried in a spray dryer 127, preferably of the Filtermate® type. Alternatively, the concentrate can be extracted as liquid product stream N1.

As shown in FIG. 2, the hydrolysate, stream J2, can be treated using a centrifuge 221 so that the proteins and long peptides, stream N2, are separated off. These are mixed with the concentrate, stream M2, of free amino acids and short peptides from the concentrator 222. The condensate, stream L2, can be used as additive water, stream E2. The concentrate, stream M2, with admixed proteins and long peptides, can be dried in a spray dryer 223 preferably of the Filtermate® type.

Unless otherwise indicated all percentage disclosures herein are given in percentages by weight.

The process is described in more detail below.

1) Raw Materials:

The raw materials for the process may consist of protein material preferably fish, fish products, shellfish, crustaceans, molluscs and by-products from fish/the fishing industry, for example, fish offal, and other marine organisms from fresh water and salt water. The different raw materials can be used singly or in a combination of products containing "enzyme material" and "protein material". The "enzyme material" is the raw material that contains the endogenous enzymes in a satisfactory amount and of a satisfactory quality. The "protein material" describes raw materials that do not contain the endogenous enzymes in a satisfactory amount and of a satisfactory quality and which must therefore be supplemented with the enzyme product in order to be able to carry out the enzyme treatment. In some cases, the enzyme material may be identical with the protein material. Previously known processes describe a combination of offal and protein material in the ratio of 1:1. The method described here makes it possible to vary this ratio in order to obtain the desired result in the end product.

The raw materials meet the statutory requirements for starting products for the production of foods. Previously, the raw materials have been classified as scrap by legislation and definitions. Through good logistics and process routines it will be possible in this case to have the raw material approved as a foodstuff. This permits production on an industrial scale and the use of the product in the food and/or pharmaceuticals industry.

2) Pre-Treatment of the Raw Materials:

The raw materials are pumped in from a tank, through a grinding system, which gives the desired combination of the materials. The grinding gives a larger working surface for the enzymes and it releases the enzymes of the raw materials more quickly.

Oil/fat from the raw materials can be recovered before the enzyme process is started. Here, for example, a cold recovery of the oil could be used.

Cold recovery of oil can be done by:
1. centrifuging the raw materials and separating liquid and solid particles into two different fractions;
2. separating the oil from the liquid phase;
3. mixing the solid phase and the heavy phase from the separation step and pumping them to the fermenter;
4. further processing the oil phase from the separation to give a finished, customer-specific product that does not require further refinement in order to attain foodstuff quality.

The materials can be pumped via either an "in-line" continuous heat exchanger or in a batch working heat exchanger to the fermentation tank. The fermentation tank may also be used for heating if this is not done in a heat exchanger before the materials are pumped in. If it is desirable to mix different types of raw materials in a certain ratio, these products can be pumped in and mixed at the same time. The amount of different raw materials can be controlled by means of flow meters and/or level control in the fermenter.

Moreover, it is possible that the raw materials are not ground or that the raw materials can avoid being mixed at the same time, in that a known amount of raw material A is pumped into a mixing tank and a known amount of raw material B is then pumped into the same tank.

It is desirable that the raw materials should be heated to a temperature that is favourable for the enzymes that are required to be most active in the hydrolysis process. This temperature range extends from 40-62° C. The optimal range in most cases will be 45-58° C. The use of different temperatures will allow the effect of different enzymes to be obtained and will permit control of the amino acid composition.

The invention provides possibilities for the recovery/separation of the fat during the process, after hydrolysis, in order to obtain a low fat content in the end product.

The fat separation can be done before and/or after coagulation of the proteins. A typical fat content of the end product is less than 0.1% in dried peptide/amino acid products.

Well-known techniques such as decantation, separation and/or chemical methods can be used for fat separation.

3) The Hydrolysis Process:

The mixture of heated raw materials is pumped into hydrolysis vessels or tanks. Warmed and pH adjusted water that has approximately the temperature at which the fermentation is to take place is added to this mixture. The amount of water can be varied according to the raw material and desired result. In the prior art an amount of 50% of the total amount was used, i.e., 50% raw material and 50% water. In the method according to the invention less water is used because of an optimisation of available enzyme and protein material and temperature and pH. This method uses an amount of from 10% to 40% added water. Optimally, the water added will be between 20 and 30%. Less added water means that the concentration of short peptides and free amino acids in the hydrolysate after hydrolysis is higher, which means a saving in process and energy costs.

The hydrolysate is kept in the fermentation tank(s) under constant stirring and pumping. The purpose of this is to improve the hydrolysis process. A failure to stir/pump the hydrolysate during the process could result in there not being sufficient control of the pH, temperature and the process itself. The hydrolysis could proceed differently in parts of the hydrolysate and some of the enzymes could be lost.

To check how far the hydrolysis has gone, amino-bound nitrogen is analysed. The analysis can be done either directly in the fermenter by means of automatic equipment or in a production laboratory using well-known techniques such as formol titration or the like. The use of time in the process can vary from 1 to 4 hours. The hydrolysis process is stopped when the percentage of free amino acids no longer increases in the hydrolysate. This is to avoid the formation of undesired ammonia, which results in a reduction of the level of utilisation of the raw materials.

It is a prerequisite for the process that it is alkaline enzymes that are at work. It is therefore essential that pH>7.00 during the hydrolysis. The pH range will be between 7.00 and 8.50. An optimal hydrolysis process is obtained at a pH of 7.60 to 8.20. If pH>8.1, but <8.4 during the whole process, free tryptophan is excluded from the amino acid spectrum. Conversely, if pH<7.6, but >7.4 during the whole process, tryptophan is maximised to the total it is possible to recover, which is determined by the raw material. If the temperature is <46° C. but >44° C. and the pH is <7.8 but >7.7 during the whole process, collagen is not dissolved to any great extent, but is obtained in the form of solid particles.

For pH adjustment of the hydrolysate different bases can be used, as for instance bone meal from previously recovered fish bones, calcium and nitrogen/nitrogen gas, but not sodium hydroxide according to aspect a).

HCl is not added to the process in the present invention. The reason for this is that unwanted salts are formed. Also, the costs of production will be higher. The prior art also describes chloroform as an additive to prevent bacterial growth. This is not used in the present process because of the short hydrolysis time. The use of chloroform on an industrial scale is not desirable, but possible.

An elevated temperature, preferably higher than 70 degrees, is used to stop the hydrolysis. This temperature increase is preferably effected using an "in-line" heat exchanger.

Coagulation of residual proteins is effected using a low pH. Phosphoric acid can then be used as an additive to lower the pH to the desired level, preferably between pH 3.2 and 5.5. After an addition of phosphoric acid, optionally in combination with heating/cooling, it will be possible to remove proteins and peptides from the hydrolysate. Naturally, other methods for denaturing proteins and peptides may also be used. For example, electrical denaturation could be used.

Known filtration techniques can be used to segment the free amino acid and short peptide content from denatured proteins and long peptides. The different weight and different chemical properties of the fractions can also be used to separate them during separation. To facilitate this, calcium phosphate, calcium hydroxide and calcium chloride may be used. This causes proteins and peptides to "stick together". Thus, they become easier to separate off owing to their increased density. The amount of chemicals added will vary, both according to the protein and peptide content and according to the content of other buffer agents in the solution.

4) Concentration:

It is then desirable to concentrate the finished hydrolysate. This is done to remove water prior to the drying process so that the capacity of the drying step is utilised to the full. A pre-concentration before drying of up to 70% dry matter (DM) is possible before crystallisation sets in.

A distillation process of the vacuum evaporation type is well suited for this purpose, but any other forms of concentration devices can be used. The vacuum evaporator concentrates the liquid at a low temperature, thereby ensuring that the peptides or amino acids are not damaged.

Evaporation can take place in the temperature range of 50-85° C. Optimally, the range will be from 65-70° C. Moreover, the hydrolysate can be passed directly to the drying step (see point 5) without passing through the concentration step or concentration may be carried out in other ways than by boiling or vacuum evaporation. Different types of filtration/membrane/osmosis plants could also perform this step.

5) Drying/Granulation:

After concentration, the product can be dried if so desired, but the product may also exist in liquid form or in any state between dry and liquid form. Drying makes the product more storage-stable, and it simplifies logistics and handling. The way in which the product is dried is of importance for the end result. A prepared peptide/amino acid product could be highly hygroscopic and is therefore a challenge as regards this process. To make the product easier to handle, it is desirable to have a granular product.

In one embodiment of this process, drying and granulation take place in two stages, but one-stage processes are of course possible. The first stage comprises drying to a powder in a spray dryer or similar, with a cooling step and then granulation by adding liquid hydrolysate.

Granulation is effected in that granulates are "constructed" by keeping the powder/product in vigorous motion using mechanically rotating blades which give the product a fluid bed like character. Then, the concentrate/hydrolysate is sprayed into this mass. This allows the gradual construction of granulates. This all takes place as a continuous process. At the end of the granulation process, dried cold air is blown across or through the granulate. The granulate is screened and the required fraction extracted. Remaining fines are recirculated for further granulation. Excessively large granulates are ground and screened again. Any newly formed fines are returned to the granulation step.

As previously mentioned, the drying and granulation process outlined above is just one of the embodiments that can be used to dry and granulate the products of the method according to the invention and anyone of ordinary skill in the art will understand that any other suitable methods can be used to obtain a similar result.

Of course, it is also possible to add various additives to the product, preferably in the granulation step.

The carrying out of the invention according to aspect c) thereof will now be described in more detail.

Figure 3:
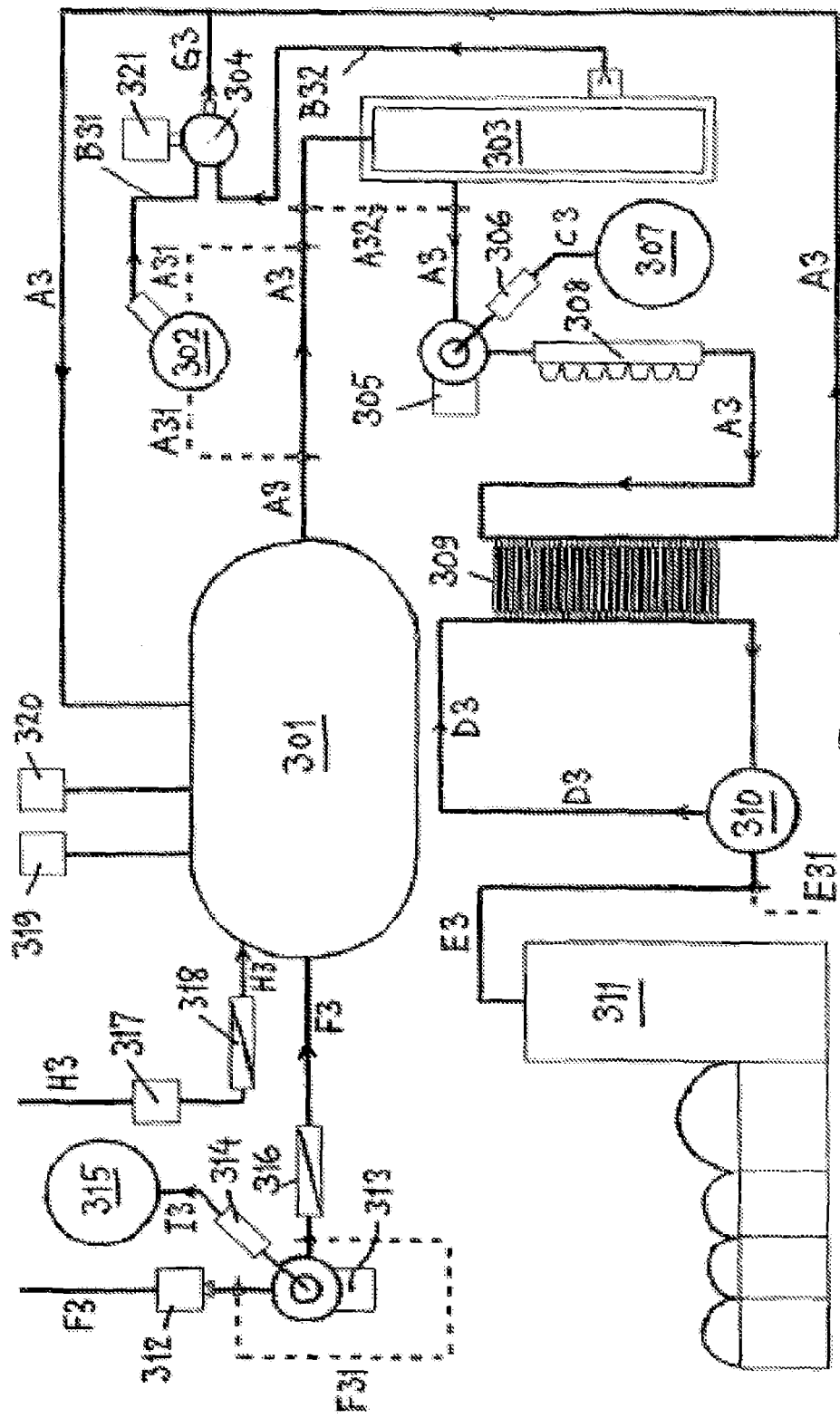
FIG. 3 shows a third embodiment of a plant in which the hydrolysis process according to aspect c) of the invention is used.

The reference numerals in FIG. 3 represent the following parts of the plant:

301=Fermenter
302=Separation unit for the removal of solid particles, preferably a screen
303=Separation unit, preferably a centrifuge of the decanter type
304=Flotation tank for separating proteins and hydroxyapatite
305=Separation unit for separating off oil, preferably a centrifuge
306=Filter unit for sterile filtration
307=Tank for oil/fat
308=Microorganism reduction unit
309=Membrane filter unit 310=Concentration unit
311=Drying unit
312=Grinding equipment
313=Centrifuge, preferably of the decanter type
314=Oil filter
315=Tank for oil recovered prior to the hydrolysis step
316=Heat exchanger for heating raw materials
317=Calcium dosing unit
318=Heat exchanger for heating the water
319=Device for supplying bone meal
320=Device for adding nitrogen
321=Container for recovered bone fraction.

In addition, FIG. 3 shows, together with the description of the plant, an embodiment of the process of the invention according to aspect c), in which the designations represent the following streams:

A3=Stream including proteins, enzymes, oil/fat, peptides and free amino acids. After the microorganism reduction unit 308, the stream does not contain any solid particles, and has a considerably reduced proportion of non-hydrolysed proteins and fat if the separation units 302 and 302 have been used;

A31=Stream if separation unit 302 is used; after the unit 302 the stream no longer contains solid particles;

A32=Stream if separation unit 303 is not used;

B31=Stream including solids removed using screen;

B32=Stream including solids separated using centrifuge;

C3=Stream including oil/fat;

D3=Stream of distillate or the like for release of permeate from the membrane filter 309;

E3=Stream of concentrated peptide-amino acid solution to the drying unit;

E31=Stream of concentrated peptide-amino acid solution to packing as a liquid product;

F3=Stream of raw materials to fermenter 301;

F31=Stream of raw materials when oil separation does not take place before the hydrolysis;

G3=Stream of non-hydrolysed proteins returning to stream A3;

H3=Stream of added water;

I3=Stream of oil recovered before the hydrolysation step.

Unless otherwise indicated, all percentage disclosures are given in percentages by weight.

The process is described in more detail below:

1) Raw Materials:

The raw materials for the process may consist of protein materials; preferably fish, fish products, shellfish, crustaceans, molluscs and by-products from fish or the fishing industry, for example, fish offal and other marine organisms from fresh water and salt water. The various raw materials can be used singly or in a combination of products containing "enzyme material and "protein material". The "enzyme material" is the raw material containing the endogenous enzymes in satisfactory quantity and of a satisfactory quality. The "protein material" describes raw materials that do not contain the endogenous enzymes in satisfactory quantity and of a satisfactory quality, and which must therefore be supplemented with the enzyme material in order to be able to carry out the enzyme treatment. In some cases, the enzyme material may be identical to the protein material. Prior art processes describe a combination of offal and protein material in the ratio 1:1. The method described in this application makes it possible to vary the ratio in order to obtain the desired result in the end product.

The raw materials meet the statutory requirements for starting products for the production of foods. Previously, the raw materials have been classified as scrap through legislation and definitions. Through good logistics and process routines, it will be possible in this case to have the raw material approved as a foodstuff. This facilitates production on an industrial scale and the use of the product in the food processing and/or pharmaceutical industry.

2) Pre-Processing of the Raw Materials:

The raw materials are pumped in from a tank, through a grinding system 312 which gives the desired combination of the materials. The grinding gives a larger working surface for the enzymes and releases the enzymes of the raw materials.

A first oil/fat from the raw materials can be recovered before the enzyme process is started. Here, for example, a cold recovery of the oil could be used.

Cold recovery of oil can be carried out by:
1. centrifuging 313 the raw materials and, separating liquid and solid particles into two different fractions;
2. separating the oil from the liquid phase, cf. 314 and 315;
3. mixing the solid phase and the heavy phase from the separation step and pumping them to the fermenter 301;
4. further processing the oil phase from the separation step to give a finished customer-specific product that does not require further refinement in order to attain foodstuff quality.

The raw materials that are added to the fermenter 301 can be stored in one or more buffer tanks after grinding. Different tanks can be used for protein material and enzyme material.

The materials can be pumped via a heat exchanger 316 to the fermentation tank 301. The fermentation tank 301 can also be used for heating if this is not done in a heat exchanger before the materials are pumped in.

Monitoring of the conditions in the fermenter 301 is done continuously, either automatically or by manual sampling. The addition of various additives is done so that the conditions for the enzymation are kept as constant as possible within the range that is optimal for the product that is to be produced.

3) Enzymation Process:

Heated raw materials or non-heated raw materials in the form of protein materials and enzyme materials are pumped into one or more emzymation tanks. Warmed and pH-adjusted water that has approximately the temperature at which the fermentation will take place is added to this mixture. The amount of water can be varied according to raw material and desired result, depending upon an optimisation of available enzyme and protein material. The pH is adjusted by the addition of, for example, nitrogen gas or bone meal.

The warmed and pH adjusted mixture of raw material F3 and water H3 will hereinafter be called "hydrolysate". The hydrolysate is kept in the fermenter tank 301, optionally under constant and vigorous stirring. The purpose of this is to enhance the enzymation process. The hydrolysate is pumped continuously through the system for removal of the desired amino acids and peptides.

To keep the conditions for the enzymation constant in the fermentation tank 301, amino-bound nitrogen, total protein content and pH are checked regularly.

Protein material and enzyme material are added as required throughout the desired duration of the process.

It is a prerequisite for the process that it is alkaline enzymes that are at work. It is therefore essential that pH>7.00 during the enzymation. The pH range will be between 7.00 and 8.50. An optimal enzymation process is obtained at a pH of 7.60 to 8.20. If pH>8.1, but <8.4 during the whole process, free tryptophan is excluded from the amino acid spectrum. Conversely, if pH<7.6, but >7.4 during the whole process, tryptophan is maximised to the total it is possible to recover, which is determined by the raw material. If the temperature is <46° C. but >44° C. and the pH is <7.8 but >7.7 during the whole process, collagen is not dissolved to any great extent, but is obtained in the form of solid particles.

Different bases, such as bone meal from earlier production, calcium and nitrogen, cf. 319 and 320, can be used for pH adjustment of the hydrolysate.

By means of the present invention according to aspect c) thereof, it is possible to continuously control the enzymation process by using different parameters in order to maintain the conditions at an optimal level.

At the end of the process, the enzyme activity must be terminated by temperature inactivation or in some other way in order to prevent ammonification.

4) Control of Microorganism Growth:

The prior art describes chloroform as an additive for preventing the growth of microorganisms, but it is preferably not used in this process. In the method according to the invention, UV or another suitable method that does not coagulate the enzymes is used to kill bacteria and fungi. This is done to prevent a substantial growth of microorganisms from consuming the liberated short peptides and the free amino acids in the formation of new proteins. Moreover, chloroform on an industrial scale is not preferred.

5) Removal of Solid Particles:

The invention involves that solid particles, over a certain size, can be removed from the hydrolysate either continuously or periodically by means of a screen system/filter. The screen system 302 can be omitted from or by-pass the system if the decanter system 303 in the next production stage handles the whole solid phase removal, or that product A3 which in the present situation is being processed, does not contain solid particles that are suitable for screening.

The removed particles B32 can then be separated according to density through a flotation process 304 so that protein residues G3 can be fed back to the fermentation tank 301. Proteins float up and can be skimmed off either mechanically or manually. The heavier material ends up at the bottom of the flotation tank.

6) Decantation of the Hydrolysate:

A decanter 303 can be used in the system before the oil separator 305 and the membrane filter 309. This is done to simplify the separation of fat from the hydrolysate in, for example, a three-phase separator and thereby reduce the strain on the subsequent membrane filter.

A separator does not work optimally if the content of solid particles is too high, which means that the sludge phase is large. The decanter is a machine constructed to separate solid particles of a larger density than the liquid of which they are a part. In the invention, it is primarily proteins that are separated, and so it is desirable to pass them back to the fermentation tank for further enzymation. The separated solid material can be floated according to the same principle as that used in the screening system. The same flotation device can be used, if desired. The decanter 303 may be omitted or disconnected from the system if the screen device that has already been mentioned handles the desired separation or that products being treated do not give protein residues that can be removed using a decanter.

7) Separation:

The hydrolysate is separated using a three-phase separator 305 or other suitable centrifuging method that is suitable for separating the lighter fat fraction from the hydrolysate. The separation of fat takes place either continuously or periodically depending on the amount of fat in the raw materials that are being processed. A particularly important feature of the present invention is that a very pure and high-quality fat fraction can be recovered because the separation can be done continuously throughout the process so that the fat released is not subjected to oxidation longer than necessary when the lipoproteins are decomposed by the hydrolysis. That the hydrolysis takes place under alkaline conditions also helps to keep the quality of the fat high, especially when nitrogen is used for pH adjustment.

8) Membrane Filtration:

The invention involves the hydrolysate being pumped through a device equipped preferably with a membrane filter 309 which functions in a manner that allows molecules of a certain size to penetrate the membranes, preferably less than 10,000 Daltons. The filtration is done so that the hydrolysate is either pumped through a plurality of tubular membranes or past a plurality of planar membranes.

The principle of osmosis is used for transport through the membranes. Concentration of the unfiltered free amino acids and peptides gives distilled water as a by-product and a part of this is fed back to the filter at approximately the same pressure as the hydrolysate on the other side of the membrane. By keeping the concentration of amino acids and peptides lower on the permeate side of the membranes, an osmosis-driven penetration through them will be maintained. The flow of hydrolysate along the membranes cleans them mechanically of deposits of protein residues and peptides that are larger than those able to penetrate the membranes.

9) Concentration:

The finished hydrolysate filtrate must then be concentrated. This is done to remove water before the drying process so that the capacity of the drying step is utilised to the full, or that the concentration level of incoming amino acids and peptides desired in a liquid product is obtained.

A distillation process of the vacuum evaporation type is well suited for this purpose, but any other forms of concentration devices can be used to remove the desired peptides and amino acids from the liquid in which they are dissolved during the membrane filtration. The vacuum evaporator 310 concentrates the liquid at a low temperature, so that the peptides/amino acids are not damaged. A prerequisite for the function of the membrane filtration in earlier stages being optimal is that the concentration device 310 is able to return a distillate that is as pure as possible. Thus, the osmosis through the membranes will be optimal. Evaporation can take place in the temperature range of +50-+85° C. Optimally, this range will be from +65-+70° C. There may be a risk of the condensate having a temperature that is too high to be passed back to the filter or the fermentation tank. If this is the case, a heat exchanger that reduces the temperature to the desired level must be used.

10) Drying:

After concentration, the product can be dried if so desired, but it may also be in the form of a liquid product or any form therebetween. Drying, cf. 311, makes the product more storage-stable, and it simplifies logistics and handling. The way in which the product is dried is of importance for the end result. A prepared peptide/amino acid product could be highly hygroscopic and is therefore a challenge as regards this process. A high temperature in the drying process will also cause the product to be of a more hygroscopic character.

Drying/granulation will take place in two stages. First, the product is dried to a powder in a spray dryer or the like, with a cooling step and then the product is granulated. Granulation is effected in that granulates are "constructed" by keeping the powder/product in vigorous motion by means of mechanical fluidisation. Then, the concentrate/hydrolysate is sprayed into this mass and the granulates are gradually built up. All this takes place in a continuous process. At the end of the granulation process dried cold air is blown across/through the granulate. This results in it being harder and more readily soluble. The granulate is then screened and the desired fraction is extracted. Particles that are too small (fines) are passed back for further granulation, whilst "oversize" particles are ground and screened again. Any newly formed fines pass back for regranulation.

Ordinary conventional spray drying could also be used, but this gives a fine powder with a large surface. This means that the product behaves in a highly hygroscopic manner and it is therefore difficult to handle it in large packages, storage etc.

Various additives can be added to the product during the granulation process. Products that are not granulated can also be produced, as can products that are not dried but simply concentrated to the desired level. Detailed Description of the Function of the Membrane Filter:

The filter 309 may be constructed of planar or tubular filter elements. The filter system is so constructed that the filtrate, which consists of protein hydrolysate from the fermenter from which solid particles and fat have been removed, but which includes an enzyme complex, can freely circulate past the retentate side of the membranes (crossflow filtering). Thus, a flow is generated along the surface of the membranes which mechanically minimises the risk of the formation of a blocking filter cake of retentate deposited on the membranes. The filtrate circulating on the retentate side of the filter membranes contains enzymes which break down the proteins and large peptides that become lodged on and in the membranes but are too large to penetrate the membranes to the permeate side. The enzymes are prevented from penetrating the membranes if the choice of membrane is made so that maximum molecule size of the permeate is 9,800 Daltons. Thus, non-decomposed proteins are blocked and a protein-free sterile product is obtained.

The choice of a membrane with blocking of smaller molecules will result in a product having smaller peptides and a higher percentage of free amino acids.

On the permeate side, a stream of preferably water is made to pass along the membranes, corresponding to that on the permeate side. The pressure may be equal on both sides of the membranes, osmosis driving the permeate through the membranes. Dissolution takes place in the liquid circulating on the permeate side.

The requirement for the osmosis to work is that the concentration of amino acids and peptides is higher on the retentate side of the membranes. This is achieved by the distillate from the concentration plant being the liquid that is made to circulate on the permeate side of the membrane. In principle, this can be described as a reverse diafiltration where it is on the permeate side that a pure water additive is used.

The concentration of the permeate can be done using another membrane filter arranged for reverse osmosis (RO). The function of the membrane filter will be the same.

A series of filters can be used to separate the different fractions, with regard to maximum peptide size, but in the succeeding filters there is no help from the enzyme complex to keep the filter membranes free of filter cake on the retentate side. It may be advantageous to filter in one stage in order to prevent blocking.

Values that have been obtained in laboratory tests using a dialysis membrane of standard hose-shaped type used in the hospital area produced by the manufacturer Spectrum Laboratories:

In tests Spectra/Por 1 Regenerated Cellulose (RC) with Molecular Weight Cut-Off (MWCO) of 6,000 to 8,000 Daltons (6 k to 8 k MWCO) were used. The flux through these membranes with a total of DM (dry matter) on the retentate side of 14.7% at a temperature of 48.7° C. and a pH of 7.85 was 3.7 ml/cm$^2$/h at the start. After 12 hours it was 3.8 ml/cm$^2$/h and after 24 hours it was 3.8 ml/cm$^2$/h. Blocking could not be registered even at 60 hours operating time. No molecules of more than 9,000 Daltons could be identified in the permeate, with peptide size analysis before and after concentration of the total of 23 liters of liquid with 36% DM that was produced during the total of 60 hours. The largest peak on the spectrogram was from 410-1350 Daltons which without correction gave 42% of the spectrogram area.

What is claimed is:

1. A method for producing peptides/amino acids with a fat content of less than 0.5% by weight from a protein-containing raw material, wherein the method comprises:
    (a) grinding the protein-containing raw material;
    (b) heating the ground raw material to temperatures in the range of 40-62° C.;
    (c) adding water which has approximately the same, or the same, temperature as the raw material, and wherein the pH of the water is adjusted to 7.0-8.5;
    (d) hydrolysing the ground raw material with endogenous enzymes in order to prepare a hydrolysate;
    (e) removing solid particles and non-hydrolysed proteins which can be returned to the hydrolysis from the hydrolysate;
    (f) periodically or continually separating off fat/oil in order to obtain an oil product;
    (g) separating off the desired molecular weight fraction of peptides/amino acids by membrane filtration;
    (h) routing the portions of the hydrolysate that do not penetrate the membrane filter in step (g) back to the hydrolysis in step (d);
    (i) concentrating and optionally drying the permeate in order to obtain a distillate comprising water, and a concentrate comprising peptides/amino acids and water; and
    (j) wholly or partly returning the distillate from the concentrating to the permeate side of the membrane filter.

2. The method according to claim 1, wherein the method takes place as a closed process.

3. The method according to claim 1, wherein the method further comprises dividing the solid particles from step (e) into hydroxyapatite, protein residues and other solid particles.

4. The method according to claim 1, wherein the oil product recovered in step (f) is passed through a sterile filter, and any solid particles are removed in order to obtain a cold-processed, protein-free sterile oil.

5. A method for the hydrolysis of one or more protein-containing raw materials wherein the hydrolysis is carried out using endogenous enzymes of the one or more protein-containing material or materials, the method comprising:
    heating the one or more protein-containing raw materials;
    pumping the one or more protein-containing raw materials into a hydrolysis tank; and
    adding water having a temperature of 45-58° C. in an amount of 10-40% by weight of the total reaction mixture, wherein the mixture is constantly stirred and pumped, and wherein during the hydrolysis the pH is 7.6-8.2.

6. A method for removing peptides and amino acids from a hydrolysis mixture, wherein the hydrolysis mixture contains active enzymes, amino acids, peptides and non-converted proteins, the method comprising:

passing the hydrolysis mixture through a membrane filter, wherein amino acids and any peptides having a molecular weight less than 10,000 Daltons are filtered off and the active enzymes break down proteins that are deposited on the membrane filter.

7. Amino acids/peptides produced by the method according to claim 1, wherein the amino acids/peptides do not contain allergens and DNA traces, wherein the free amino acid content is 30-60% by weight, the fat content is less than 0.5% by weight and the salt content is less than 1% by weight.

8. Amino acids/peptides produced by the method according to claim 1, wherein the amino acids/peptides do not contain allergens and DNA traces, wherein the free amino acid content is 5-100% by weight, the fat content is less than 0.1% by weight and the salt content is less than 0.5% by weight.

9. The method according to claim 1, further comprising, before and/or after step (b):

separating oil/fat from the raw materials in order to obtain a second oil product.

10. The method according to claim 1, further comprising, before and/or after step (d):

adding a pH adjuster in order to maintain the desired pH value of 7.0-8.5 of the hydrolysate.

11. The method according to claim 1, further comprising, after step (f):

treating the hydrolysate against microorganism growth with UV.

12. The method of claim 1, wherein, at step (b), the temperature is in the range 45-58° C.

13. The method of claim 1, wherein the membrane filtration is of crossflow type.

14. The method of claim 4, wherein the solid particles comprise stearic acid.

* * * * *